(12) United States Patent
Boudeville et al.

(10) Patent No.: US 8,440,737 B2
(45) Date of Patent: May 14, 2013

(54) COMPOSITION FOR INJECTABLE CEMENT USEFUL AS BONE REPLACEMENT

(75) Inventors: Philippe Boudeville, Clapiers (FR); Michel Vert, Castelnau-le-Lez (FR); Sylvie Munier, Montpellier (FR)

(73) Assignees: Centre National de la Recherche Scientifique, Paris (FR); Universite de Montpellier 1, Montpellier (FR)

(*) Notice: Subject to any disclaimer, the term of this patent is extended or adjusted under 35 U.S.C. 154(b) by 1447 days.

(21) Appl. No.: 11/579,535

(22) PCT Filed: Apr. 29, 2005

(86) PCT No.: PCT/FR2005/001078
§ 371 (c)(1),
(2), (4) Date: Nov. 3, 2006

(87) PCT Pub. No.: WO2005/115488
PCT Pub. Date: Dec. 8, 2005

(65) Prior Publication Data
US 2008/0027455 A1 Jan. 31, 2008

(30) Foreign Application Priority Data

May 3, 2004 (FR) .................................. 04 04714

(51) Int. Cl.
*A61F 2/28* (2006.01)
*A61L 24/02* (2006.01)
*A61K 33/06* (2006.01)
*A61K 33/10* (2006.01)

(52) U.S. Cl.
USPC ........... 523/105; 523/113; 523/116; 424/423; 424/602; 424/682; 424/686

(58) Field of Classification Search .................. 523/105, 523/113, 114, 115, 116; 424/423, 602, 682, 424/686
See application file for complete search history.

(56) References Cited

U.S. PATENT DOCUMENTS

| 5,997,624 | A  | * | 12/1999 | Chow et al. ...................... 106/35 |
| 6,593,394 | B1 |   | 7/2003  | Li et al. |
| 6,692,563 | B2 | * | 2/2004  | Zimmermann ............... 106/696 |
| 2002/0034275 | A1 | * | 3/2002 | Abalin et al. .................. 376/189 |
| 2003/0199615 | A1 | * | 10/2003 | Chaput et al. ..................... 524/2 |
| 2005/0142211 | A1 | * | 6/2005 | Wenz ............................ 424/603 |

FOREIGN PATENT DOCUMENTS
WO WO 03/103734 12/2003

OTHER PUBLICATIONS
International Search Report dated Sep. 23, 2005.

* cited by examiner

*Primary Examiner* — Michael Pepitone
(74) *Attorney, Agent, or Firm* — Merchant & Gould

(57) ABSTRACT

The invention relates to a composition for injectable cement, comprising a mineral sold phase, a separate liquid phase and, optionally, microparticles of a biocompatible and biodegradable polymer. The mineral solid phase comprises a mixture of powders with the molar composition: $(CP)_6$ $(CaO)_y$ $(SrCO3)_z$, [CP being $CaHPO_4 2H_2O$, $CaHPO4$, $Ca_{1-x}Sr_x$- $HPO_4$, an equimolar mixture of $bis(Ca(H_2PO_4)_2$, $H_2O$ and CaO, or a mixture of two or three of said compounds] and y+z=4?1. The liquid phase comprises pure apyrogeneic water or a saline aqueous solution with pH 4 to 9. The ratio L/P [volume of liquid phase/mass of solid mineral phase] is at least 0.4 ml/g. The above is of application as bone replacement.

24 Claims, 3 Drawing Sheets

COMPOSITION FOR INJECTABLE CEMENT USEFUL AS BONE REPLACEMENT

CROSS-REFERENCE TO RELATED APPLICATIONS

This application is a National Stage Application of PCT/FR2005/001078, filed 29 Apr. 2005, which claims benefit of Application No. 0404714, filed 3 May 2004 in France. To the extent appropriate, a claim of priority is made to each of the above disclosed applications.

The present invention relates to a composition for injectable cement of use as bone replacement.

Calcium phosphate hydraulic cements are of use as bone replacements. Cements which can be injected using a syringe are particularly desired insofar as they make it possible to fill in a bone defect by surgery which is not very invasive. In addition, the strengthening and the stabilization of an osteoporotic bone tissue can be carried out solely by injection, without excision or destruction of the residual bone matrix.

BACKGROUND OF THE INVENTION

It is known to prepare a calcium phosphate hydraulic cement by mixing water or an aqueous phase with a powder composed of various precursors of calcium phosphate. For example, M. Bohner (Injury, 2000, 31:S-D37-47) describes the preparation of hydraulic cements from a mixture of a calcium phosphate possessing an acidic nature and of a calcium phosphate possessing a basic nature. Such cements are available commercially, in particular under the names Bone-Source®, Cementek®, Calcibon® or ChronOS Inject®. One of the disadvantages of these cements is that they are resorbed very slowly.

Various routes have been explored to improve the rate of resorption of hydraulic cements.

It has been envisaged to partially replace the calcium of the calcium phosphate compounds by strontium. Thus, GB-943678 discloses calcium phosphate hydraulic cements obtained from a powder composed of a mixture of anhydrous $M(H_2PO_4)_2$ and of an oxide of a metal M' (it being possible for M and M' to represent, independently of one another, Zn, Mg, Ba, Ca, Al, Cd or Sr) in approximately equal proportions by weight, said powder being mixed with water in a water/powder ratio of 0.15 ml/g. The only compositions illustrated are $Ca(H_2PO_4)_2+ZnO$, on the one hand, $Zn(H_2PO_4)_2+ZnO$. The cements obtained from these powders have a compressive strength of greater than 100 MPa and setting times of the order of 8-10 min. However, the inventors of the present invention have carried out tests with a mixture of anhydrous calcium bis(dihydrogenphosphate) $(Ca(H_2PO_4)_2)$ and of CaO with an L/P ratio of 1 ml/g, in order to obtain a paste which can be worked under the conditions disclosed in GB-943678, and the results obtained show that the compressive strength after 24 h is less than 1 MPa. The general teaching of this document thus does not make it possible to obtain a cement exhibiting the required properties (good compressive strength, high setting rate) for any combination of M and M'. In addition, in the specific case in which one of the metals M or M' would be Sr (not illustrated in GB943678), neither the compound $Sr(H_2PO_4)_2$ nor the compound SrO would make possible the formation of a mean porosity.

Leroux, et al. (Bioceramics, 13, Trans Tech Publications, Switzerland, 2001, 235-238) describe a cement comprising up to 4.3% by weight of Sr, corresponding to a final cement composition $Ca_{9.75}Sr_{0.25}(PO_4)_6(OH)_2$. This composition can be obtained by adding strontium nitrate $Sr(NO_3)_2$ to the liquid phase of the abovementioned Cementek® cement, the solid phase of which is composed of a mixture of $\alpha$-$Ca_3(PO_4)_2$ (or $\alpha$-TCP), of tetracalcium phosphate (or TTCP) and of glycerophosphate. Here again, the specific choice of the strontium precursor does not make it possible to obtain a mean porosity.

Another solution envisaged for improving the rate of resorption of the bone replacement is based on the principle that the presence of interconnected macropores in the calcium phosphate material promotes passive resorption by dissolution of the implant, by allowing it to be percolated by biological fluids, and active resorption by osteoclasts, by allowing them to penetrate into the macropores which are sufficiently large, that is to say greater than 100 µm in size. U.S. Pat. No. 6,547,866 discloses porous calcium phosphate materials obtained by adding, to the composition, compounds which release a gas during the setting of the cement (carbonate+citric acid, which release $CO_2$, hydrogen peroxide, which releases $O_2$). However, the pores obtained have a relatively small mean size and the mechanical strength is reduced. In addition, it has been proposed to prepare calcium phosphate materials by addition to the composition, before the setting thereof, of a water-soluble compound of the $NaHCO_3$, $Na_2HPO_4$, sucrose or mannitol type (Markovic et al., Bioceramics, Trans Tech Publications, Switzerland, 2001, 773-775; Takagi and Chow, J. Mater. Sci. Mater. Mad., 2001, 13, 135-139). The dissolution of these sugars interferes with the setting of the cement, which greatly reduces the crushing strength.

The addition of particles or of fibers of a biodegradable polymer has also been envisaged. Simon et al. (J. Orthop. Res., 2002, 25, 473-482) describe cements of the Bone-Source® type, obtained from TTCP, which is a basic phosphate, and from anhydrous dicalcium phosphate (DCPA), which is an acidic phosphate, and poly(lactide-co-glycolide) PLAGA microspheres, the rapid decomposition of said polymer giving a macroporosity. However, the mineral part is not degraded in vitro after 90 days.

Xu H et al. (Biomaterials, 2002, 23, 193-202, and Biomaterials, 2004, 25, 1029-1037) describe a calcium phosphate cement (BoneSource®) comprising fibers of Vicryl® or a net of Vicryl®, which is a bioresorbable polymer very rich in glycolic acid. Due to the presence of the fibers or of the net, this cement cannot be injected.

Ruhe et al. (J. Bone Joint Surg., 2003, 85, 75-81) describe a Calcibon® ($\alpha$-TCP+DCPA+$CaCO_3$+HA) cement comprising PLAGA microspheres charged with rhBMP-2, which diffuses from the polymer (HA denoting hydroxyapatite). However, the authors indicate that the introduction of the polymer very strongly reduces the crushing strength, which changes from 38.6 to 6.4 MPa (value lower than that of trabecular bone≈10 MPa). However, the authors do not indicate whether, after 28 days in pH 7 buffer solution, the polymer and/or the mineral part of the cement are decomposed.

SUMMARY OF THE INVENTION

The aim of the present invention is to provide an injectable cement which can be used as bone replacement and which exhibits an injection time and a setting time compatible with injection techniques, good compressive strength after injection and a high rate of resorption after injection.

This is why a subject matter of the present invention is a composition for injectable cement which is biocompatible and biodegradable, a process for the preparation of an injectable cement from said composition, the injectable cement obtained and its use by injection into a bone material, in particular in the treatment of osteoporosis, in spondylotherapy or for filling in bone after a fracture or an excision.

The composition for injectable cement according to the invention comprises a separate mineral solid phase and a separate liquid phase and optionally microparticles of a biocompatible and biodegradable polymer, the mineral solid phase being composed of a mixture of powders having the molar composition $(CP)_6(CaO)_y(SrCO_3)_z$, in which CP represents calcium hydrogenphosphate dihydrate $CaHPO_4 \cdot 2H_2O$ (DCPD), anhydrous calcium hydrogenphosphate $CaHPO_4$ (DCPA), anhydrous mixed calcium strontium hydrogenphosphate $(Ca_{1-x}Sr_x)HPO_4$, an equimolar mixture of calcium bis(dihydrogenphosphate)monohydrate $Ca(H_2PO_4)_2 \cdot H_2O$ (MCPM) and of calcium oxide CaO, or a mixture of two or three of these compounds, and $y+z=4\pm1$;

the liquid phase being composed of pure pyrogen-free water or of an aqueous saline solution having a pH of 4 to 9;

the L/P [volume of liquid phase/weight of mineral solid phase] ratio being at least equal to 0.4 ml/g.

The L/P ratio is preferably from 0.4 ml/g to 0.7 ml/g in the absence of polymer microparticles (more particularly from 0.5 to 0.6 ml/g). The L/P ratio is at least equal to 0.6 ml/g in the presence of polymer microparticles.

The mixture of MCPM and of CaO is a precursor of DCPD. The two constituents of the mixture react with precipitation of DCPD in the 3 minutes subsequent to bringing the solid phase into contact with the liquid phase.

The compositions in which at least a portion of the constituent CP represents DCPD are preferred. Preference is very particularly given to the compositions in which CP is composed solely of DCPD.

When the liquid phase is a saline solution, it can be composed of:

a solution comprising from 0.4 to 1 mol/l of a mixture of $NaH_2PO_4$ and of $Na_2HPO_4 \cdot 12H_2O$ (NaP buffer), for example a solution of pH 7 comprising 0.75 mol/l of phosphate;

an aqueous solution having a pH of 4 to 8 and comprising from 0.4 to 1 mol/l of a mixture of $NaH_2PO_4$ and of sodium glycerophosphate hexahydrate $Na_2PO_4C_3H_7O_2 \cdot 6H_2O$ (NaGP buffer), for example a solution of pH 6.6 comprising 0.75 mol/l of phosphate;

an aqueous solution comprising from 0.4 to 1.5 mol/l of a mixture of $NH_4H_2PO_4$ and of $(NH_4)_2HPO_4$ (NH4P buffer), for example a solution of pH 6.65 comprising 0.75 mol/l of phosphate.

BRIEF DESCRIPTION OF THE DRAWINGS

FIG. 2a shows a microsphere after splitting the sample; the numerous vacuoles present on the microsphere indicate the advanced hydrolytic degradation of the polymer after 33 days, which occurs even within the samples of composite cement and not only at the surface.

FIG. 2b shows a portion of 3 microspheres (upper left-hand corner, lower left-hand corner and upper right-hand corner) surrounding a cellular mineral region having a high mean porosity (pore diameter of 5 to 100 µm); this mean porosity is also seen around the microsphere of FIG. 2a.

DETAILED DESCRIPTION OF THE PREFERRED EMBODIMENTS

Figure 1:
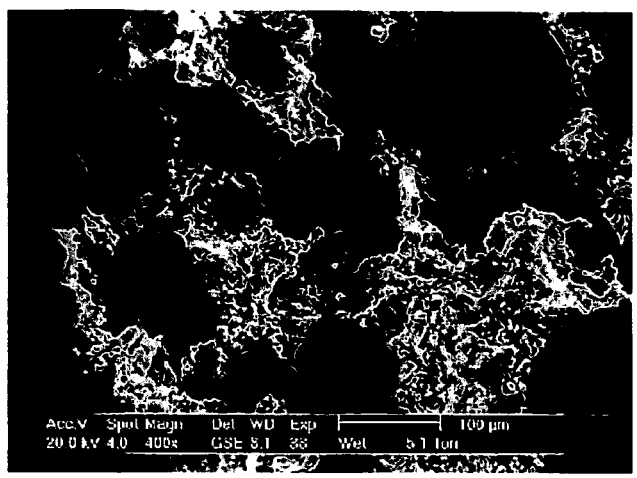
FIG. 1 is an image obtained by observation using an environmental scanning electron microscope (ESEM) and represents the surface of the sample 3A 1 day after mixing the liquid phase and the solid phase. The polymer microspheres are still not degraded and are perfectly visible, embedded in the mineral matrix.

In a specific embodiment, the composition for injectable cement additionally comprises microparticles of a biocompatible and biodegradable polymer. Mention may be made, by way of example, of an intrinsically amorphous PLAGA polymer composed of L-lactic units, D-lactic units and glycolic units. Mention may also be made of a PLA polymer composed solely of L-lactic units. Other polymers, degradable by hydrolysis or biodegradable by action of living cells, can be used, for example copolymers of lactic acid, of glycolic acid and of gluconic acid which are disclosed in particular in FR-2 765 228 and which are degraded more rapidly than PLAGA under identical conditions. The ratio by weight of the polymer constituent to the mineral solid phase is between 20 and 60%, preferably of the order of 40%.

In a preferred embodiment of a composition for injectable cement which comprises polymer microparticles, the composition comprises a third phase composed of said microparticles. In another embodiment, the mineral solid phase additionally comprises said microparticles.

The presence of polymer microparticles in a composition for injectable cement does not bring about any reduction in the crushing strength of the cement after setting, the strength remaining greater than that of trabecular bone.

The microparticles are preferably microspheres. They can optionally comprise a chemical or biological compound which will be released during the degradation of the polymer after the in vivo implantation of the injectable cement. The diameter of the microspheres can be between 50 and 500 µm, preferably between 125 and 250 µm.

When the composition for injectable cement comprises polymer microparticles, it is preferable to increase the value of the L/P ratio in order to keep the total injection time at a satisfactory level. The L/P ratio is in this case at least equal to 0.6 ml/g. The purpose of the increase in the proportion of the liquid phase is to compensate for the absorption of a certain amount of liquid by the polymer and to keep sufficient liquid phase in the mineral solid phase for it to remain injectable.

The process for the preparation of the injectable cement from the composition according to the invention consists in bringing the solid phase (which optionally comprises polymer microparticles) and the liquid phase of the composition for injectable cement into contact, at the time of the use of the injectable cement, under the aseptic conditions required for the injection of bone replacements. The process can be carried out using any conventional device for the preparation of a cement. Mention may be made, for example, of the mixing device disclosed in U.S. Pat. No. 5,549,380, which makes it possible to introduce the liquid phase into the solid phase by suction at the time when the mixture has to be prepared. Use may also be made of a flexible two-compartment bag in which each compartment comprises one of the phases of the composition, the compartments being separated by a seal which is broken at the time when the mixture has to be prepared, allowing the liquid phase to pass into the compartment comprising the solid phase.

When the composition for injectable cement comprises polymer microparticles in the form of a 3rd phase, this 3rd phase is added to the paste obtained immediately after the liquid phase and the mineral solid phase have been brought into contact.

In the absence of polymer microparticles, the paste obtained immediately after bringing the two phases of the composition according to the invention into contact is composed of $(CP)_6$, $(CaO)_y$ and $(SrCO_3)_z$, water and the salts possibly present in the liquid phase, the respective amounts being such that:

the $(CP)/(CaO)/(SrCO_3)$ molar ratio is $6/y/z$ with $y+z=4\pm1$, the L/P (volume of liquid phase/weight of mineral solid phase) ratio is from 0.4 to 0.7 ml/g, more particularly from 0.5 to 0.6 ml/g.

The embodiment in which CP comprises $CaHPO_4 \cdot 2H_2O$ is preferred, in particular in which CP is composed solely of $CaHPO_4 \cdot 2H_2O$.

The injectable paste thus obtained has an injection time and a setting time which are compatible with use as bone replacement by injection. The term "injection time" is intended to mean the time during which a composition remains completely injectable after mixing the liquid phase and the solid phase. The term "setting time" is understood to mean the period of time necessary for the composition, after mixing the two phases, to become solid (standard ASTM C191).

The setting time of the cement is shorter if an NaP or NH4P buffer solution is used. The injection time is longer with an NaGP buffer solution.

The injectable cement according to the invention gives, after injection, a material composed predominantly of modified hydroxyapatite $Ca_{10-x}Sr_x(PO_4)_6(OH)_2$, which additionally comprises a small amount of octacalcium phosphate and possibly traces of unreacted $SrCO_3$. It exhibits a porosity characterized by pores having a mean size of the order of 20 to 50 μm originating essentially from the decomposition of $SrCO_3$ during the setting of the cement. This mean porosity makes possible better penetration of the fluids inside the cement and an increase in the exchange specific surface, which facilitates the diffusion of the ions originating from the dissolution of the components of the cement and which thus brings about better passive resorption.

When the composition for injectable cement additionally comprises microparticles of bioresorbable biodegradable polymer, the material obtained after injection comprises the same constituents as above, and also polymer microparticles, the polymer/mineral solid phase ratio by weight being between 20 and 60% (preferably of the order of 40%) and the initial L/P ratio being at least equal to 0.6 ml/g. In addition, it is found that the abovementioned mean porosity exists to a greater degree around the polymer microparticles, which generate acidic compounds during the hydrolytic degradation, which constitute an advantage for in vivo degradation. After the time necessary for the resorption of the polymer, it additionally exhibits a network of interconnected macropores having a mean size of greater than 100 μm.

When the polymer is the abovementioned PLAGA, the spherical PLAGA microparticles can be obtained by adding a solution of PLAGA in dichloromethane to an aqueous poly (vinyl alcohol) (PVA) solution and by keeping the mixture stirred for a certain period of time, and then by recovering the particles by filtration. Nonspherical PLAGA particles can be obtained by cryomilling.

In solution, whether buffered or not, a cement according to the invention continuously releases strontium ions and can thus act as system for the controlled and prolonged release of strontium ions, which activate bone reconstruction by stimulation of the osteoblasts.

When the cement comprises microspheres of a polymer, said polymer first degrades slowly and then much more rapidly from 3 weeks. This degradation of the polymer can be taken advantage of by charging the latter with an active principle (for example, an antibiotic) or with a protein (for example a growth factor), in order also to obtain prolonged release of this active principle, the action of which may be complementary to that of the strontium. It is possible in particular advantageously to combine the particles of PLAGA or of other degradable polymers with antitumor agents, in particular in the case of the filling of post-tumoral bone excisions.

The presence of the $Sr^{2+}$ ions renders the cement more radioopaque, which facilitates the monitoring by radioscopy during the injection of the cement into the bone material.

An injectable cement according to the invention which does not comprise polymer particles can advantageously be used for the stabilization and/or strengthening of osteoporotic bone by injection into the residual bone matrix, for example in spondylotherapy, the presence of $Sr^{2+}$ promoting osteogenesis.

An injectable cement comprising polymer microparticles can be used in the filling of bone defects resulting from an excision or from a fracture. The release of $Sr^{2+}$ and the macroporosity created by the degradation of the polymer in vivo stimulates bone regrowth. In addition, owing to the fact that strontium has a radioactive isotope which is used in the treatment of certain forms of cancer having bone tropism, the inactive strontium carbonate can be completely or partially replaced by radioactive strontium-89 carbonate for the filling after excision of a bone tumor, with optionally an antimitotic substance charged to the biodegradable polymer.

The present invention is illustrated by the following examples, to which, however, it is not limited.

Example 1

Injectable Cement without Polymer Microbeads

A powder mixture was prepared which has the following molar composition: 6 DCPD, 2.5 CaO, 1.5 $SrCO_3$.

The following were prepared:
an aqueous solution of the NaP buffer type having the composition $NaH_2PO_4 + Na_2HPO_4 \cdot 12H_2O$ (0.75M) and a pH of 7;
an aqueous solution of the NaGP buffer type having the composition $NaH_2PO_4 + Na_2PO_4C_3H_7O_2 \cdot 6H_2O$ (0.75M) and a pH of 6.6;
an aqueous solution of the $NH_4P$ buffer type having the composition $NH_4H_2PO_4 + (NH_4)_2HPO_4$ (0.75M) and a pH of 6.65.

Two compositions for cement were prepared with each of the buffer solutions by mixing the solution and the powder in a liquid phase/mineral solid phase L/P ratio (in ml/g) of 0.5 and 0.6.

The characteristics of the compositions obtained are given in table I below.

TABLE 1

| | Sample | | | | |
|---|---|---|---|---|---|
| | 1A | 1B | 1C | 1D | 1E |
| Liquid phase | NaP | NaP | NaGP | NaGP | NH4P |
| L/P | 0.5 | 0.6 | 0.5 | 0.6 | 0.5 |
| Compressive strength (MPa) | 21.0 ± 2.8 | 17.6 ± 1.8 | 19.5 ± 2.3 | 17.6 ± 3.2 | 18.0 ± 0.5 |
| Diametral compressive strength (MPa) | 1.6 ± 0.7 | 1.2 ± 0.16 | 2.3 ± 0.4 | 1.5 ± 0.1 | 1.5 ± 0.2 |
| Initial setting time (min) | | 16 | | | |
| Final setting time (min) | 14 | 19 | 19 | 30 | 15 ± 1 |
| Injection time $t_{100\%}$ (min) | 6 ± 0.5 | 12 ± 1 | 13 ± 1 | 21 ± 3 | 9 ± 1 |
| Maximum temperature achieved (° C.) | 41.5 | | 39.2 | | 40.5 |
| Expansion during the setting (%) | 0.5 | | 0.1 | | 0.6 ± 0.1 |

The comparison of the results shows that the nature of the liquid phase does not affect the compressive strength. However, the nature of the liquid phase and the L/P ratio have an effect on the final setting time and on the total injection time. The NaP or NH4P buffers will be chosen when rapid setting is desired. An NaGP buffer will be chosen when ease of injection is desired.

Example 2

Preparation of PLAGA Microbeads

Use was made of an intrinsically amorphous $PLA_{37.5}GA_{25}$ polymer theoretically composed of 37.5% of L-lactic units and 25% of glycolic units. Said polymer has a glass transition temperature of 49° C., a storage modulus E'≈3.5 GPa, a loss modulus E"≈120 MPa and a loss angle δ≈2.0° (at T=37° C. and F=500 Hz). The $^1$H NMR spectra give an overall composition of $PLA_{36.8}GA_{26.4}$. Gel permeation chromatography gives a single peak corresponding to a molar mass $\overline{M}w$ of 111 100 with a distribution $\overline{M}w/\overline{M}n=1.9$.

4 g of said polymer were dissolved in 50 ml of dichloromethane and the solution thus obtained was added, with mechanical stirring of 900 rpm, to 1 l of an aqueous solution comprising 5 g of poly(vinyl alcohol) (PVA). Stirring was maintained at ambient temperature for 4 h and then the spheres formed were recovered by filtration on a sintered glass funnel (porosity 3), washed with distilled water and then dried on a Büchner. After leaving overnight in a desiccator, the spheres were sieved and separated according to their size. The spheres having a diameter of 125-250 μm (hereinafter denoted by S2 microspheres) were recovered for subsequent use.

Example 3

Cement Composition with Polymer Microbeads for Different Proportions of Polymer

The procedure of example 1 corresponding to the samples 1A and 1C was repeated but while replacing a portion of the mineral solid phase "6 DCPD, 2.5 CaO, 1.5 $SrCO_3$" with a polymer in the form of S2 microspheres of example 2. In each case, three tests were carried out while varying the amount of polymer. It was found that a polymer/mineral phase ratio by weight of 40% is sufficient for the microspheres to be in contact, that is to say to obtain interconnected macroporosities after degradation of the polymer.

The microspheres were incorporated in the phosphate powder and then the mixture was incorporated in the liquid phase.

The compressive strength was determined for the compositions obtained respectively with NaP and with NaGP and 40% of S2 polymer microspheres and was compared with that of the equivalent composition without microspheres. The results are given in table 2 below. In all cases, the compressions were determined after 24 h at 37° C. and 100% relative humidity.

TABLE 2

| | Sample | | | |
|---|---|---|---|---|
| | 1A | 3A | 1C | 3C |
| Liquid phase | NaP | NaP | NaGP | NaGP |
| L/P | 0.5 | 0.5 | 0.5 | 0.5 |
| Polymer/mineral phase (% by weight) | 0 | 40 | 0 | 40 |
| Compressive strength (MPa) | 21.0 ± 2.8 | 19.6 ± 2 | 19.5 ± 2.3 | 19.2 ± 2 |

It is also apparent that the addition of polymer microbeads has virtually no effect on modifying the compressive strength.

Figure 2A:
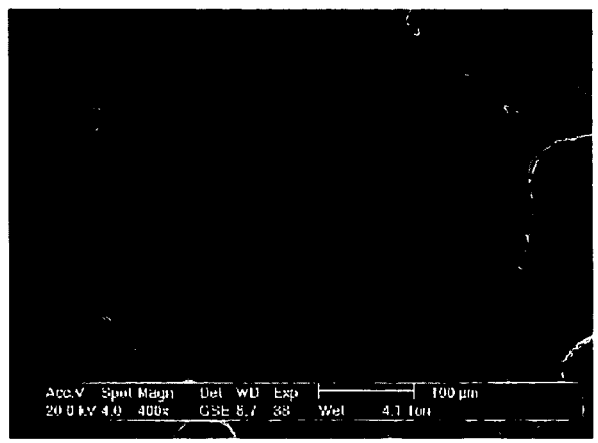
FIGS. 2a and 2b are images obtained by observation using an environmental scanning electron microscope (ESEM) and represent the core of the sample 3A after 33 days and before the complete resorption of the microspheres.
Figure 2B:
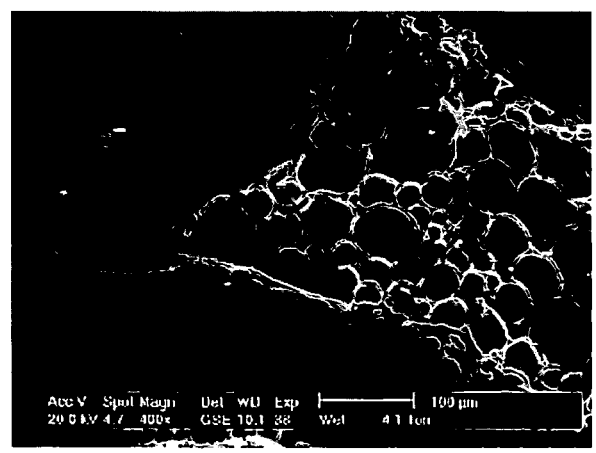

FIGS. 1, 2a and 2b represent images obtained by observation using an environmental scanning electron microscope (ESEM).

FIG. 1 represents the surface of the sample 3A 1 day after mixing the liquid phase and the solid phase. The polymer microspheres are still not degraded and are perfectly visible, embedded in the mineral matrix.

FIGS. 2a and 2b represent the core of the sample 3A after 33 days and before the complete resorption of the microspheres. FIG. 2a shows a microsphere after splitting the sample; the numerous vacuoles present on the microsphere indicate the advanced hydrolytic degradation of the polymer after 33 days, which occurs even within the samples of composite cement and not only at the surface.

FIG. 2b shows a portion of 3 microspheres (upper left-hand corner, lower left-hand corner and upper right-hand corner) surrounding a cellular mineral region having a high mean porosity (pore diameter of 5 to 100 μm); this mean porosity is also seen around the microsphere of FIG. 2a.

It is thus apparent that, both at the surface and at the core of the sample of composite cement 3A, the distribution of the microspheres is homogeneous and the microspheres touch, which will give interconnected macropores after resorption of the polymer.

Example 4

Cement Composition with Polymer Microbeads for Different L/P Ratios

The procedure of example 1 was repeated for each of the samples 1A to 1D but while replacing a portion of the mineral solid phase with a polymer in the form of S2 microspheres in order to have a polymer/mineral phase ratio by weight of 40%. The microspheres were incorporated in the same way as in example 3. Various properties of the four samples obtained were compared and the result is given in table 3 below. The compressions were determined after 24 h at 37° C. and 100% relative humidity.

TABLE 3

| | Sample | | | | | |
|---|---|---|---|---|---|---|
| | 4A = 3A | 1A | 4B | 1B | 4C = 3C | 4D |
| Liquid phase | NaP | NaP | NaP | NaP | NaGP | NaGP |
| L/P | 0.5 | 0.5 | 0.6 | 0.6 | 0.5 | 0.6 |
| Polymer/mineral phase (% by weight) | 40 | 0 | 40 | 0 | 40 | 40 |
| Compressive strength (MPa) | 19.6 ± 2 | 21 ± 2.8 | | 17.6 ± 1.8 | 19.2 ± 2 | 12.8 ± 2.5 |
| Total injection time $t_{100\%}$ (min) | 0 | 6 | 5 | 12 | 5 | 7 |

It was found that the addition of microbeads greatly reduces the setting time and the 100% injection time. For the sample 4A (NaP buffer), the $t_{100\%}$ is virtually zero, whereas it is 6 min for the equivalent cement without microbeads (sample 1A). Likewise, for the sample 1B without microbeads, the $t_{100\%}$ which is 12 min, changes to 5 min for a content of microbeads of 40%. The replacement of the NaP buffer by the NaGP buffer improves the injectability of the composite cement.

Example 5

Degradation of a Composite Cement of Example 3

The samples of a cement without microbeads 1A (hereinafter denoted by "cement") and of a cement with microbeads 3A (hereinafter denoted by "composite") were immersed, 1 hour after their preparation, in 10 ml of water or of a sodium phosphate buffer, pH 7, 0.05M.

In a first series, the samples remained in the same solution for one month, the pH of the solution being measured daily. Each week, their surfaces were examined by ESEM and the possible presence of oligomers originating from the degradation of the PLAGA was looked for by capillary zone electrophoresis.

Figure 3:
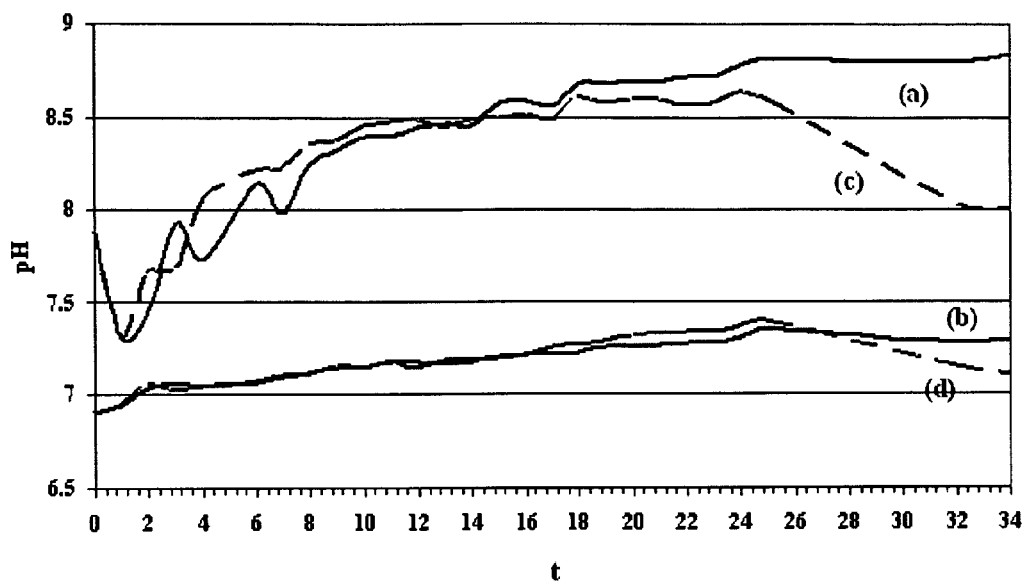
FIG. 3 is a graph demonstrating the change in the pH. The time d (in days) is indicated on the abscissa and the pH is indicated on the ordinate.

For the cement samples and for the composite samples, the pH of the water slowly increases with the contact time to stabilize after 4 weeks at a value of 8.8 (for the cement) or decrease (for the composite). The same behavior is observed in phosphate buffer but with a weaker variation. The change in the pH is represented in FIG. 3. The time d (in days) is indicated on the abscissa and the pH is indicated on the ordinate. The correspondence between the samples and the steeping solutions, on the one hand, and the curves, on the other hand, is as follows:

| Curve a | cement in water |
| Curve b | cement in the phosphate buffer |
| Curve c | composite in water |
| Curve d | composite in the phosphate buffer. |

The fall in the pH after the 24th day visible in curves c and d indicates the accelerated degradation of the polymer microspheres in water as in the sodium phosphate buffer, which acidifies the medium, with the result of accelerating the degradation of the mineral part.

The release of calcium ions from the cement and from the composite is very low, both in water and in phosphate buffer (limit of detection possibility). The analysis of a solution unchanged for one month gives concentrations of 11 ppm in the buffer and 18 ppm in water, i.e. a mean per day of 0.4 to 0.6 ppm.

In a second series, the solution was changed each day and the concentration of strontium, calcium and phosphate ions was measured.

The release of phosphate ions into water from the cement and from the composite is only significant on the first days. It is very low on the following days (approximately 0.5 ppm/day). The phosphate ions released in a large amount on the first days originate from the buffer used as liquid phase, as has been shown for the cement composed solely of DCPD and of CaO (S. Munier et al., Bioceramics, 16, Key Engineering Materials, Vol. 254-259, 2004, pp. 615-618, Trans Tech Publications, Switzerland).

Figure 4:
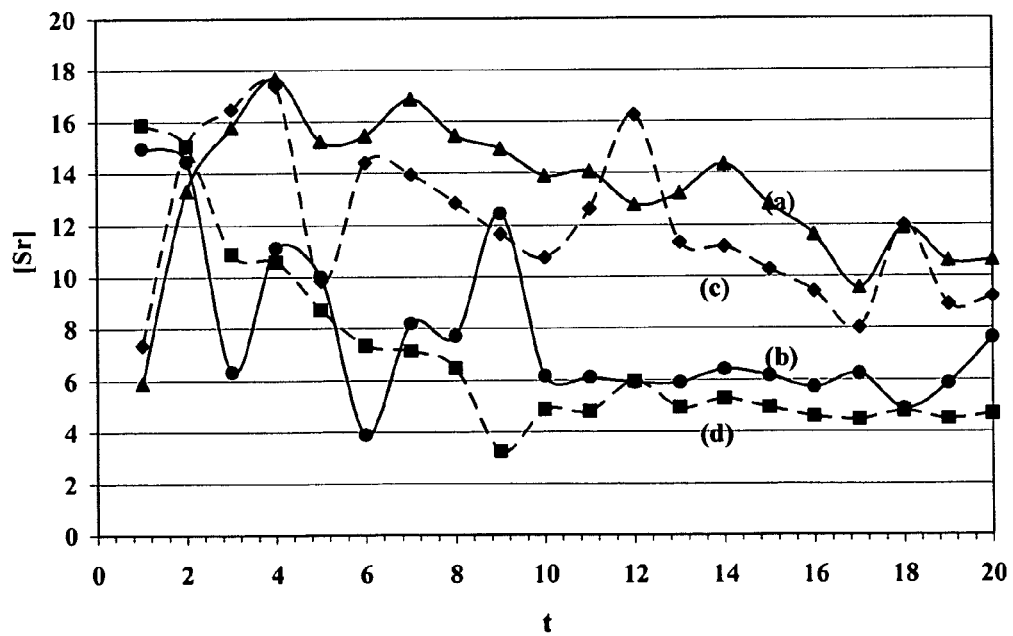
FIG. 4 is a graph providing curves representing the change in the concentration of $Sr^{2+}$ ions in an immersion bath changed each day. The time t (in days) is given on the abscissa and the concentration of $Sr^{2+}$ ions [Sr] in ppm/day is given on the ordinate.

The release of strontium ions from the cement and from the composite is much greater than that of the calcium ions, both in water and in phosphate buffer. It is continuous and stabilizes around 5 ppm in phosphate buffer and 10 ppm in water. This release is not statistically different starting from the composite or starting from the cement. The probability factor P, determined according to the ANOVA 1 method available on the Excel® software from Microsoft, is equal to 0.16, although the presence of PLAGA microspheres reduces the amount of strontium which can be released. However, this release is statistically lower in a phosphate buffer than in water (P=0.008). The curves in FIG. 4 represent the change in the concentration of $Sr^{2+}$ ions in an immersion bath changed each day. The time t (in days) is given on the abscissa and the concentration of $Sr^{2+}$ ions [Sr] in ppm/day is given on the ordinate. The immersion bath is either pure pyrogen-free water or a phosphate buffer composed of a 0.05 mol/l solution of a mixture of $NaH_2PO_4$ and of $Na_2HPO_4 \cdot 12H_2O$ of pH 7.

The correspondence between the samples and the steeping solutions, on the one hand, and the curves, on the other hand, is as follows:

| Curve a) | marked by ▲ | cement in water |
| Curve b) | marked by ● | cement in the phosphate buffer |
| Curve c) | marked by ◆ | composite in water |
| Curve d) | marked by ■ | composite in the phosphate buffer |

Figure 5:
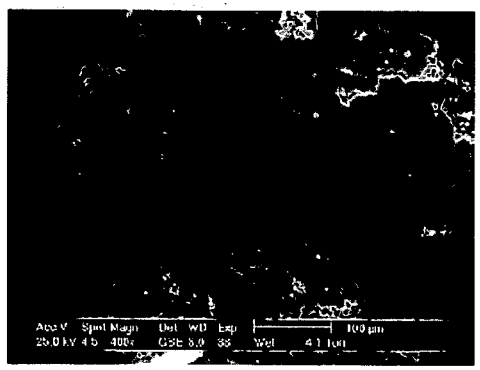
FIG. 5 is an image obtained by observation using an environmental scanning electron microscope (ESEM) and represents the appearance of the composite cement showing the condition of the spheres after degradation for 11 days (left-hand photograph) and 18 days (right-hand photograph).
Figure 5:
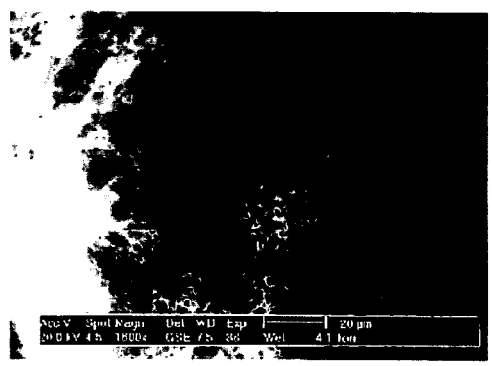

The presence of the oligomers (G, L, $G_2$, L/G, G/L, $L_2$), which indicates degradation of the PLAGA polymer to the soluble monomer or dimer stage, is really only demonstrated from the twenty-fourth day, which date corresponds to the beginning of decrease in the pH of the solutions in the presence of composite, although observation by ESEM shows a very marked change in the surface of the microspheres from the 11th day (cleavage of the long chains to give shorter chains). FIG. 5 represents the appearance of the composite cement showing the condition of the spheres after degradation for 11 days (left-hand photograph) and 18 days (right-hand photograph). The comparison with FIG. 1 clearly shows the change in the microspheres, which are very distinct after 1 day, which exhibit irregularities after 11 days and which exhibit a spongy appearance after 18 days. The presence of oligomers and of monomers and the fall in the pH after 24 days indicate an accelerated degradation of the polymer starting from the 24th day: the polymer swells, which resulted in the bursting of the blocks after 45 days.

What is claimed is:

1. A composition for preparing an injectable cement comprising a separate mineral solid phase and a separate liquid phase and optionally microparticles of a biocompatible and biodegradable polymer;
the mineral solid phase comprising a mixture of powders having the molar composition $(CP)_6(CaO)_y(SrCO_3)_z$ wherein $y+z=4\pm1$ and,
in which CP is selected from the group consisting of calcium hydrogenphosphate dihydrate, anhydrous calcium hydrogenphosphate, anhydrous mixed calcium strontium hydrogenphosphate, an equimolar mixture of calcium bis(dihydrogenphosphate)monohydrate and of calcium oxide, and mixtures thereof;
the liquid phase being composed of pure pyrogen-free water or of an aqueous saline solution having a pH of 4 to 9;
the L/P (volume of liquid phase/weight of mineral solid phase) ratio being at least equal to 0.4 ml/g.

2. The composition as claimed in claim 1, wherein CP represents calcium hydrogenphosphate dihydrate.

3. The composition as claimed in claim 1, wherein CP is a mixture comprising calcium hydrogenphosphate dihydrate.

4. The composition for injectable cement as claimed in claim 1, wherein the liquid phase is a solution comprising from 0.4 to 1 mol/l of a mixture of $NaH_2PO_4$ and of $Na_2HPO_4.12H_2O$.

5. The composition for cement as claimed in claim 1, wherein the liquid phase is a solution comprising from 0.4 to 1 mol/l of a mixture of $NaH_2PO_4$ and of sodium glycerophosphate hexahydrate $Na_2PO_4C_3H_2O_2.6H_2O$.

6. The composition for injectable cement as claimed in claim 1, wherein the liquid phase is an aqueous solution comprising from 0.4 to 1.5 mol/l of a mixture of $NH_4H_2PO_4$ and of $(NH_4)_2HPO_4$.

7. The composition for injectable cement as claimed in claim 1, wherein the mineral solid phase comprises microparticles of a biocompatible and biodegradable polymer.

8. The composition for injectable cement as claimed in claim 1, wherein it comprises a third phase composed of microparticles of a biocompatible and biodegradable polymer.

9. The composition for injectable cement as claimed in claim 7, wherein the polymer is an intrinsically amorphous PLAGA polymer composed of L-lactic units, D-lactic units and glycolic units, or a PLA polymer composed solely of L-lactic units, or a copolymer of lactic acid, of glycolic acid and of gluconic acid.

10. The composition for injectable cement as claimed in claim 7, wherein the ratio by weight of the polymer to the mineral solid phase is between 20 and 60%.

11. The composition for injectable cement as claimed in claim 1, wherein at least a portion of the strontium carbonate is radioactive strontium-89 carbonate.

12. The composition for injectable cement as claimed in claim 1 not comprising polymer microparticles, wherein the L/P ratio is from 0.4 ml/g to 0.7 ml/g.

13. The composition for injectable cement as claimed in claim 1 comprising polymer microparticles, wherein the L/P ratio is greater than or equal to 0.6 ml/g.

14. A process for the preparation of an injectable cement from a composition as claimed in claim 1, wherein the process comprises bringing the mineral solid phase and the liquid phase of the composition into contact, at the time of the use of the injectable cement, under aseptic conditions required for injection of bone replacements.

15. The process as claimed in claim 14, wherein the solid phase comprises microparticles of a biocompatible and biodegradable polymer.

16. The process as claimed in claim 14, wherein the composition comprises a third phase composed of microparticles of a biocompatible and biodegradable polymer, said third phase being added after the mineral solid phase and the liquid phase have been brought into contact.

17. An injectable cement comprising:
$(CP)(CaO)(SrCO_3)$, wherein CP is selected from the group consisting of calcium hydrogenphosphate dihydrate, anhydrous calcium hydrogen-phosphate, anhydrous mixed calcium strontium hydrogenphosphate, an equimolar mixture of calcium bis(dihydrogenphosphate)monohydrate and of calcium oxide, and mixtures thereof,
a liquid phase being composed of pure pyrogen-free water or of an aqueous saline solution having a pH of 4 to 9, and
optionally salts,
the respective amounts in the cement being such that:
the $(CP)/(CaO)/(SrCO_3)$ molar ratio is $6/y/z$ with $y+z=4\pm1$,
the liquid (volume)/solid (weight) ratio is from 0.4 to 0.7 ml/g.

18. The injectable cement as claimed in claim 17, wherein CP represents calcium hydrogenphosphate dihydrate.

19. An injectable cement comprising:
$(CP)(CaO)(SrCO_3)$, wherein CP is selected from the group consisting of calcium hydrogenphosphate dihydrate, anhydrous calcium hydrogen-phosphate, anhydrous mixed calcium strontium hydrogenphosphate, an equimolar mixture of calcium bis(dihydrogenphosphate)monohydrate and of calcium oxide, and mixtures thereof,
polymer microparticles,
a liquid phase being composed of pure pyrogen-free water or of an aqueous saline solution having a pH of 4 to 9, and
optionally salts,
the respective amounts in the cement being such that:
the $(CP)/(CaO)/(SrCO_3)$ molar ratio is $6/y/z$ with $y+z=4\pm1$,
the liquid (volume)/solid (weight) ratio before addition of the polymer microparticles is greater than or equal to 0.6 ml/g;
the polymer/mineral solid phase ratio by weight is between 20 and 60%.

20. The injectable cement of claim 17, wherein the liquid (volume)/solid (weight) ratio is from 0.5 to 0.6 ml/g.

21. A method of treating osteoporosis comprising administering the injectable cement of claim 17 to a patient in need thereof.

22. A method of spondylotherapy comprising administering the injectable cement of claim 17 to a patient in need thereof.

23. A method of treatment of bone fractures or excisions comprising filling in a bone subsequent to the fracture or excision in a patient in need thereof with the injectable cement of claim 17.

24. A composition for preparing an injectable cement consisting of a separate mineral solid phase and a separate liquid phase and optionally microparticles of a biocompatible and biodegradable polymer;
- the mineral solid phase comprising a mixture of powders having the molar composition $(CP)_6(CaO)_y(SrCO_3)$, wherein $y+z=4\pm1$ and,
  - in which CP is selected from the group consisting of calcium hydrogenphosphate dihydrate, anhydrous calcium hydrogenphosphate, anhydrous mixed calcium strontium hydrogenphosphate, an equimolar mixture of calcium bis(dihydrogenphosphate)monohydrate and of calcium oxide, and mixtures thereof;
- the liquid phase being composed of pure pyrogen-free water or of an aqueous saline solution having a pH of 4 to 9;

the L/P (volume of liquid phase/weight of mineral solid phase) ratio being at least equal to 0.4 ml/g.

* * * * *